United States Patent
Yasueda et al.

(10) Patent No.: US 6,274,634 B1
(45) Date of Patent: Aug. 14, 2001

(54) AQUEOUS SUSPENSION PREPARATIONS WITH EXCELLENT REDISPERSIBILITY

(75) Inventors: Shin-ichi Yasueda, Takarazuka; Keiichi Matsuhisa, Himeji; Hideo Terayama, Itami; Katsuhiro Inada, Kobe, all of (JP)

(73) Assignee: Senju Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 09/423,558

(22) PCT Filed: Apr. 30, 1998

(86) PCT No.: PCT/JP98/01998

§ 371 Date: Nov. 10, 1999

§ 102(e) Date: Nov. 10, 1999

(87) PCT Pub. No.: WO98/51281

PCT Pub. Date: Nov. 19, 1998

(30) Foreign Application Priority Data

May 14, 1997 (JP) .................................... 9-124166

(51) Int. Cl.[7] ................... A61K 31/56; A61K 31/505; A61K 31/21
(52) U.S. Cl. ..................... 514/781; 514/171; 514/912
(58) Field of Search ................... 514/781, 912, 514/169–182

(56) References Cited

U.S. PATENT DOCUMENTS

| | | | |
|---|---|---|---|
| 5,124,392 | * 6/1992 | Robertson et al. | 514/169 |
| 5,244,673 | * 9/1993 | Gejkova et al. | 424/486 |
| 5,366,985 | * 11/1994 | Nakayama et al. | 514/369 |
| 5,516,808 | * 5/1996 | Sawaya | 514/781 |
| 5,624,962 | * 4/1997 | Takeuchi et al. | 514/772.2 |
| 5,679,665 | * 10/1997 | Bergamini et al | 514/171 |

FOREIGN PATENT DOCUMENTS

| | | |
|---|---|---|
| 0 531 529 | 3/1993 | (EP) . |
| 99/37286 | 7/1999 | (WO) . |

* cited by examiner

Primary Examiner—Shep K. Rose
(74) Attorney, Agent, or Firm—Wenderoth, Lind & Ponack, L.L.P.

(57) ABSTRACT

The aqueous suspension can be prepared by incorporating, in an aqueous suspension of a hardly soluble drug, a water-soluble polymer within the concentration range from the concentration at which the surface tension of the aqueous suspension of the drug begins to decrease up to the concentration at which the reduction in surface tension ceases. The resulting aqueous suspension shows ready redispersibility and will not undergo aggregation of dispersed particles or caking. Because of its good redispersibility, the suspension is useful as a parenteral preparation, eye drops, nasal drops, a preparation for oral administration, a lotion or the like.

9 Claims, 1 Drawing Sheet

AQUEOUS SUSPENSION PREPARATIONS WITH EXCELLENT REDISPERSIBILITY

TECHNICAL FIELD

The present invention relates to an aqueous suspension with good redispersibility.

BACKGROUND ART

In preparing, for instance, an ophthalmic preparation, nasal preparation or parenteral preparation containing a medicinal compound hardly soluble in water, it is presumable that the drug be suspended in an aqueous medium to give an aqueous suspension. When such aqueous suspension is stored for a long period, the drug occurring as dispersed particles (hereinafter sometimes referred to merely as dispersed particles) tends to undergo aggregation, resulting in increases in size of dispersed particles or sedimentation of dispersed particles and further in secondary aggregation of the dispersed particles that have settled, for example caking. Therefore, efforts have been devoted to prevent the aggregation or sedimentation of dispersed particles as far as possible or, when such aggregation or sedimentation cannot be prevented, to obtain suspensions capable of readily regaining their original state.

One method so far proposed comprises making dispersed particles smaller, decreasing the difference between the specific gravity of dispersed particles with of the dispersion medium and increasing the viscosity of the dispersion medium to thereby prevent the particles from settling. In such cases, for increasing the viscosity of the dispersion medium, the concentration of the suspending agent and/or thickening agent, such as a water-soluble polymer, has generally been selected within the range of 0.2 to 5.0% (w/v: weight/volume).

However, even when the concentration of the suspending agent and/or thickening agent is within such range, the sedimentation of particles cannot entirely be prevented. The problem which remains is that dispersed particles settle and deposit, causing caking, resulting in failure of uniform redispersion.

Another method which is conceivable comprises making drug particles greater in size to thereby improve their redispersibility. In the case of an ophthalmic preparation, however, greater particle sizes may cause a foreign matter sensation or eye irritation upon instillation. In the case of a nasal preparation, greater particle sizes make it impossible to apply it from a spray bottle. In the case of an injection, it is a drawback that it cannot be administered through a needle.

DISCLOSURE OF INVENTION

Among the drugs recently developed and producing pharmacological effects of value, many are hardly soluble ones. For supplying these in the form of aqueous preparations such as ophthalmic, nasal, parenteral and other preparations, it is unavoidable in many instances to employ the aqueous suspension form. However, the prior art aqueous suspensions have a redispersibility problem; in many instances, it is difficult to restore suspensions uniform in concentration without a long time of shaking to effect redispersion. Thus, the advent of aqueous drug suspensions which can be readily prepared and have good redispersibility has been waited for. Accordingly, it is the primary object of the present invention to provide an aqueous suspension showing good redispersibility without undergoing aggregation of dispersed particles or caking.

The present inventors made intensive investigations to solve the above problems and, as a result, found that there is a certain relationship between the surface tension of an aqueous suspension and the redispersibility thereof. Based on such finding, they have now completed the present invention.

The invention is thus concerned with an aqueous suspension comprising a hardly soluble drug together with a water-soluble polymer within the concentration range from the concentration at which the surface tension of the drug suspension begins to decrease up to the concentration at which the reduction in surface tension ceases.

As will be shown later herein in Test Example 1, the surface tension of an aqueous suspension begins to decrease with the increase in the amount of a water-soluble polymer added thereto. Upon continuation of the addition, the reduction in surface tension ceases and, thereafter, a substantially constant surface tension is maintained. On the contrary, the redispersibility of the dispersed particles of an aqueous suspension becomes good at the point at which the surface tension of the aqueous suspension begins to decrease as a result of addition of the water-soluble polymer, and the good redispersibility is maintained until the reduction in surface tension ceases. Thereafter, as the reduction in surface tension ceases and the surface tension becomes constant, the redispersibility of the dispersed particles becomes gradually worsened.

Where no water-soluble polymer is present, the dispersed particles aggregate together and float on the surface of the suspension and therefore no uniform suspension can be prepared.

The concentration of a water-soluble polymer at which the surface tension of an aqueous drug suspension begins to decrease and the concentration of the water-soluble polymer at which the reduction in surface tension ceases generally increase according to the contents of the hardly soluble drug used in the aqueous suspension but vary depending on the physical properties, chemical structure, and concentration and particle size of the hardly soluble drug, among others. The water-soluble polymer concentration at which the surface tension of the drug suspension begins to decrease is generally 0.00001 to 0.01% (w/v), preferably 0.00005 to 0.005% (w/v), while the water-soluble polymer concentration at which the reduction in surface tension of the suspension ceases is generally 0.0001 to 0.1% (w/v), preferably 0.001 to 0.01% (w/v).

The aqueous suspension of the present invention is generally prepared at a water-soluble polymer concentration within the range of 0.00001 to 0.1% (w/v), preferably 0.00005 to 0.05% (w/v), more preferably 0.0001 to 0.01 w/v %.

The ratio of the water-soluble polymer to the hardly soluble drug is generally 0.0001 to 0.2 part by weight, preferably 0.0005 to 0.1 part by weight, more preferably 0.0005 to 0.05 part by weight of the former to 1 part by weight of the latter.

The water-soluble polymer to be used in the practice of the present invention may be any pharmaceutically acceptable water-soluble polymer, irrespective of type or category. Cellulose derivatives and water-soluble polyvinyl polymers are suited for use, however.

As the cellulose derivatives, there may be mentioned, for example, hydroxypropylmethylcellulose, methylcellulose, hydroxyethylcellulose and hydroxypropylcellulose. Particularly preferred among them are hydroxypropylmethylcellulose and methylcellulose.

As the water-soluble polyvinyl polymers, there may be mentioned, among others, polyvinylpyrrolidone K25, polyvinylpyrrolidone K30, polyvinylpyrrolidone K90, and polyvinyl alcohol (partial hydrolyzed product, complete hydrolyzed product).

As used herein, the "hardly soluble drug" includes, within the meaning thereof, those drugs which belong, in solubility classification, to one of the groups "sparingly soluble", "slightly soluble", "very slightly soluble" and "practically insoluble" as so defined in the Japanese Pharmacopoeia. Thus, it includes all drugs that can be provided in the final dosage form of aqueous suspensions.

As specific examples of the hardly soluble drug to be used in the practice of the present invention, there may be mentioned steroidal antiinflammatory agents, antiinflammatory analgesics, chemotherapeutic agents, synthetic antibacterial agents, antiviral agents, hormones, anticataract agents, neovascularization inhibitors, immunosuppressants, protease inhibitors, and aldose reductase inhibitors, among others. The steroidal antiinflammatory agents include, among others, cortisone acetate, hydrocortisone acetate, betamethasone, prednisolone, fluticasone propionate, dexamethasone, triamcinolone, loteprednol, fluorometholone, difluprednate, momethasone furoate, clobetasol propionate, diflorasone diacetate, diflucortolone valerate, fluocinonide, amcinonide, halcinonide, fluocinolone acetonide, triamcinolone acetonide, flumetasone pivalate and clobetasone butyrate. The antiinflammatory analgesics include, among others, alclofenac, aluminopropfen, ibuprofen, indomethacin, epirizole, oxaprozin, ketoprofen, diclofenac sodium, diflunisal, naproxen, piroxicam, fenbufen, flufenamic acid, flurbiprofen, floctafenine, pentazocine, metiazinic acid, mefenamic acid and mofezolac. The chemotherapeutic agents include, among others, sulfa drugs such as salazusulfapyridine, sulfadimethoxine, sulfamethizole, sulfamethoxazole, sulfamethopyrazine and sulfamonomethoxine, synthetic antibacterial agents such as enoxacin, ofloxacin, cinoxacin, sparfloxacin, thiamphenicol, nalidixic acid, tosufloxacin tosilate, norfloxacin, pipemidic acid trihydrate, piromidic acid, fleroxacin and levofloxacin, antiviral agents such as aciclovir, ganciclovir, didanosine, didovudine and vidarabine, and antifungal agents such as itraconazole, ketoconazole, fluconazole, flucytosine, miconazole and pimaricin. The hormones include, among others, insulin zinc, testosterone propionate and estradiol benzoate. The anticataract agents include, among others, pirenoxine and the like. The neovascularization inhibitors include, among others, fumagillin and derivatives thereof. The immunosuppressants include, among others, ciclosporin, rapamycin and tacrolimus. The protease inhibitors include, among others, [L-3-trans-ethoxycarbonyloxiran-2-carbonyl]-L-leucine (3-methylbutyl)amide (E-64-d) and the like. The aldose reductase inhibitors include, among others, 5-(3-ethoxy-4-pentyloxyphenyl)thiazolidine-2,4-dione and the like.

The concentration of the hardly soluble drug to be used in the practice of the invention may vary according to the drug species, indication, dosage and other factors. Generally, however, it is 0.01 to 10.0% (w/v), preferably 0.1 to 5.0% (w/v).

The aqueous suspension of the present invention may contain, in addition to the hardly soluble drug and water-soluble polymer, known compounds such as a buffer (e.g. carbonate salt, phosphate salt, acetate salt, glutamic acid, citrate salt, ε-aminocaproic acid), an isotonizing agent (e.g. glycerol, mannitol, sorbitol, propylene glycol, sodium chloride, potassium chloride, boric acid), a stabilizer (e.q. sodium edetate, sodium citrate), a surfactant (e.g. polysorbate 80, polyoxyethylene(60) hydrogenated castor oil, tyloxapol, benzalkonium chloride), a preservative (p-hydroxybenzoate and it's analogs, benzalkonium chloride, benzethonium chloride, chlorobutanol), a pH control agent (e.g. hydrochloric acid, sodium hydroxide, phosphoric acid), and other additives.

In cases where an additive which may influence the surface tension of the aqueous suspension, for example a surfactant, is used, it is preferred that the surface tension measurement be made prior to addition of the surfactant and the surfactant be added after selection of the concentration of the water-soluble polymer.

The pH of the aqueous suspension of the present invention is not critical but, generally, it is 4 to 9, preferably 5 to 8. It is preferred that the surface tension be selected according to the intended pH of the aqueous suspension.

The aqueous suspension of the invention has good redispersibility without involving aggregation or caking of dispersed particles and, therefore, can be used with advantage as, for example, an ophthalmic preparation, a preparation for nasal application, an injection, a preparation for oral administration or a lotion.

BEST MODE FOR CARRYING OUT THE INVENTION

Figure 1:
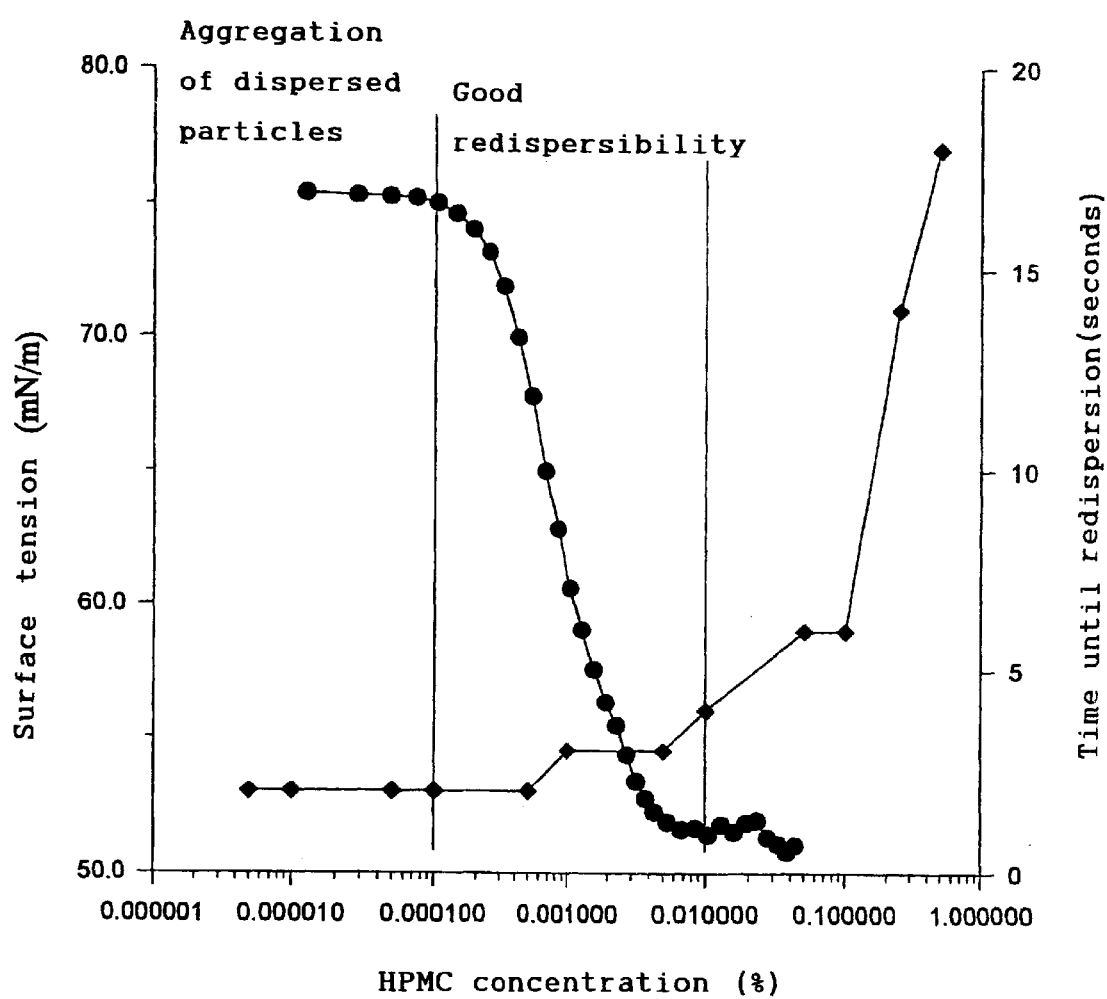
FIG. 1 is a graphic representation of the relationships between the HPMC concentration and the surface tension and redispersion time for a 0.1% (w/v) fluorometholone suspension as found in Test Example 1. In the figure, -●- indicates the surface tension, and -◆- indicates the redispersion time.

The following test examples and working examples illustrate the invention in further detail. They are, however, by no means limitative of the scope of the invention.

TEST EXAMPLE 1 Surface tension-redispersibility test

[Method]

Solutions containing a suspending agent in concentrations ranging from 0.000001 to 0.5 w/v % were first prepared. A test drug was added to the solutions to prepare aqueous suspensions. The surface tension of each aqueous suspension thus prepared was measured with the Du Noüy tension meter K122 (Krüss). The suspensions were then filled into 5 ml colorless polypropylene bottles and allowed to stand at 25° C. for 4 days. Each bottle was caused to spin (60 rpm) on the variable mix rotor VMR-5 (60 rpm, manufactured by Iuchi) and the time required for redispersion was measured. In addition, the condition of the redispersed particles was visually examined.

As the suspending agent, hydroxypropylmethyl cellulose [Metolose 60SH (TC-5E); manufactured by Shin-Etsu Chemical Co., Ltd.; hereinafter abbreviated as HPMC], methylcellulose (Metolose SM-25; manufactured by Shin-Etsu Chemical Co., Ltd.; abbreviated as MC), or polyvinylpyrrolidone (K30; manufactured by BASF; abbreviated as PVP) was used. As the test drug, fluorometholone 0.05 w/v % or 0.1 w/v % or indomethacin 0.2 w/v % or 1.0 w/v % was used.

[Results]

(1) Relationship of the concentration of HPMC to the surface tension and redispersion time of fluorometholone 0.1 w/v % suspension The relation between the surface tension and redispersibility of a fluorometholone 0.1 w/v % suspension is shown in FIG. 1.

In the case of HPMC, the surface tension began to decline at 0.0001 w/v % and the decrease in surface tension almost ceased at 0.01 w/v. On the other hand, within the concentration range of 0.000005 to 0.0001 w/v % HPMC, the time required for redispersion was 2 seconds but the dispersed particles aggregated and floated, failing to give a uniform suspension. Over the range of 0.0001 to 0.01 w/v % HPMC, the redispersion time was less than 4 seconds and a unitorm suspension was obtained without aggregation of suspended particles. When the concentration of HPMC was over 0.01 w/v %, the redispersion time exceeded 5 seconds, indicating that the redispersibility is adversely affected.

The preferred ratio of HPMC to fluorometholone was found to be 0.001 to 0.1 part by weight of the former to 1 part by weight of the latter.

(2) Relationship of the concentration of HPMC to the surface tension of fluorometholone 0.05 W/v % suspension With HPMC, the surface tension began to decline at 0.0001 w/v % (surface tension: 65.1 mN/m) and the decrease in surface tension almost ceased at 0.002 w/v % HPMC (surface tension: 50.5 mN/m). The time required for redispersion of fluorometholone in this concentration range of HPMC was about 6 seconds and the condition of the dispersion was satisfactory.

The preferred ratio of HPMC to fluorometholone was 0.002 to 0.04 part by weight of the former to 1 part by weight to the latter.

(3) Relationship of the concentration of MC to the surface tension and redispersion time of fluorometholone 0.1 w/v % suspension With the concentration of MC being 0.0001 w/v % and below, the surface tension was almost constant at 72.5 mN/m. The surface tension began to decline at 0.0001 w/v % MC and the decrease in surface tension almost ceased at 0.01 w/v %, when a tension value of 54.5 mN/m was recorded. On the other hand, when the concentration of MC was 0.0001 w/v % or less, the redispersion time was as short as 2 seconds or less but the dispersed particles aggregated and floated, failing to give a uniform suspension. Within the concentration range of 0.0001 to 0.01 w/v % MC, the necessary redispersion time was 9 to 10.7 seconds, with redispersion taking place rapidly without aggregation of dispersed particles. When the concentration of MC was over 0.01 w/v %, the redispersion time was found to be close to 20 seconds, with redispersibility being adversely affected.

The preferred ratio of MC to fluorometholone was 0.001 to 0.1 part by weight of the former to 1 part by weight of the latter.

(4) Relationship of the concentration of HPMC to the surface tension and redispersion time of indomethacin 0.2 w/v % suspension When the concentration of HPMC was less than 0.0001 w/v %, the surface tension was almost constant at 72 mN/m. The surface tension began to decline at 0.0001 w/v % HPMC and the decrease in surface tension almost ceased at 0.01 w/v % HPMC, with a tension value of 48 mN/m being recorded. On the other hand, when the concentration of HPMC was below 0.0001 w/v %, the redispersion time was as short as 7 seconds or less but the dispersed particles aggregated and floated, failing to give a uniform suspension. Within the concentration range of 0.0001 to 0.01 w/v % HPMC, the redispersion time was 6.3 to 8.3 seconds, with the drug being rapidly redispersed without aggregation. When the concentration of HPMC was over 0.01 w/v %, the redispersibility was found to deteriorate, with the redispersion time exceeding 12 seconds.

The preferred ratio of HPMC to indomethacin was 0.0005 to 0.05 part by weight of the former to 1 part by weight of the latter.

(5) Relationship of the concentration of HPMC to the surface tension and redispersion time of indomethacin 1.0 w/v % suspension When the concentration of HPMC was below 0.0005 w/v %, the surface tension was almost constant at 72.73 mN/m. The surface tension began to decline at 0.0005 w/v % HPMC and the decrease in surface tension almost ceased at 0.005 w/v %, at which level a tension value of 49.7 mN/m was recorded. On the other hand, when the concentration of HPMC was less than 0.0005 w/v %, the redispersion time was not more than 7 seconds but the dispersed particles aggregated and floated, failing to give a uniform suspension. Within the concentration range of 0.0005 to 0.005 w/v % HPMC, the redispersion time was 7.3 to 16 seconds, with the drug particles being rapidly redispersed without aggregation. When the concentration of HPMC exceeded 0.005 w/v %, the redispersion time was increased to more than 20 seconds, with the redispersibility deteriorating.

The preferred ratio of HPMC to indomethacin was 0.0005 to 0.005 part by weight of the former to 1 part by weight of the latter.

(6) Relationship of the concentration of PVP to the surface tension of fluorometholone 0.05 w/v % suspension The surface tension began to decline at 0.0002 w/v % PVC (surface tension: 72.3 mN/m) and the decrease in surface tension almost ceased at 0.001 w/v % (surface tension: 69.5 mN/m).

The preferred ratio of PVP to fluorometholone was 0.004 to 0.02 part by weight of the former to 1 part by weight of the latter.

(7) Relationship of the concentration of PVP to the surface tension of fluorometholone 0.1 w/v % suspension When the concentration of PVP was less than 0.0003 w/v %, the surface tension was almost constant at 72.5 mN/m. The surface tension began to decline at 0.0003 w/v % and the decrease in surface tension almost ceased at 0.002 w/v % where a tension value of 69.5 mN/m was recorded. The time necessary for redispersion of fluorometholone in this concentration range was about 6 seconds and the condition of the dispersion was satisfactory. When the concentration of PVP was in excess of 0.002 w/v %, the redispersion time was prolonged to 18 seconds or longer, with the redispersibility being found to deteriorate.

The preferred ratio of PVP to indomethacin was 0.003 to 0.02 part by weight of the former to 1 part by weight of the latter.

The above results indicate that although the surface tension of the aqueous suspension is dependent on the kind of water-soluble polymer added and the kind and concentration of hardly soluble drug, suspensions of hardly soluble drugs with good redispersibility can be prepared within the concentration range of the water-soluble polymer from the level where the surface tension begins to decline to the level where the decrease in surface tension ceases, regardless of the kind of water-soluble polymer.

TEST EXAMPLE 2 Redispersibility test under accelerated conditions

[Method]

Ophthalmic preparations were prepared according to Examples 2 and 4 presented below and each preparation was filled in a 5 ml polypropylene bottle. After the bottle was centrifuged at 200 G for 10 minutes for forced sedimentation of the suspended particles, it was caused to spin (60 rpm) on the variable mix rotor VMR-5 (60 rpm, Iuchi) and the redispersion time was measured.

[Results]

The redispersion times of the ophthalmic preparations of Examples 2 and 4 were 4 seconds and 7 seconds, respectively. Gross observation of each redispersed suspension showed a uniform dispersion of fine particles.

The above results indicate that in the case of the aqueous suspension according to the invention, its redispersibility is well maintained even under the rugged condition of forced sedimentation of the particles by centrifugation and is not affected by the buffer and preservative ingredients, either.

EXAMPLE 1
Ophthalmic preparation

| | |
|---|---|
| Fluorometholone | 0.1 g |
| Methylcellulose | 0.0006 g |
| Sodium chloride | 0.85 g |
| Disodium hydrogenphosphate dodecahydrate | 0.1 g |
| Benzalkonium chloride | 0.005 g |
| 0.1 N Hydrochloric acid | q.s. to make pH 7.0 |
| Purified water | q.s. to make 100 ml. |

Methylcellulose was dissolved in about 80 ml of purified water by effecting dispersion with warming, followed by cooling to room temperature. Sodium chloride, Disodium hydrogenphosphate dodecahydrate and benzalkonium chloride were added for dissolution. The pH was adjusted to 7 by adding hydrochloric acid. Fluorometholone was added and uniform suspension was effected using a homogenizer. Purified water was added to make the whole volume 100 ml. A fluorometholone suspension ophthalmic preparation was thus prepared.

EXAMPLE 2
Ophthalmic preparation

| | |
|---|---|
| Fluorometholone | 0.05 g |
| Methylcellulose | 0.0003 g |
| Sodium chloride | 0.85 g |
| Sodium dihydrogen phosphate dihydrate | 0.1 g |
| Benzalkonium chloride | 0.005 g |
| 0.1 N Sodium hydroxide | q.s. to make pH 7.0 |
| Purified water | q.s. to make 100 ml. |

A fluorometholone suspension ophthalmic preparation was prepared in the same manner as in Example 1.

EXAMPLE 3
Ophthalmic preparation

| | |
|---|---|
| Fluorometholone | 0.02 g |
| Methylcellulose | 0.0001 g |
| Sodium chloride | 0.65 g |
| Disodium hydrogenphosphate dodecahydrate | 0.1 g |
| Benzalkonium chloride | 0.005 g |
| 0.1 N Hydrochloric acid | q.s. to make pH 7.0 |
| Purified water | q.s. to make 100 ml. |

A fluorometholone suspension ophthalmic preparation was prepared in the same manner as in Example 1.

EXAMPLE 4
Ophthalmic preparation

| | |
|---|---|
| Fluorometholone | 0.05 g |
| Polyvinylpyrrolidone K30 | 0.0015 g |
| Sodium chloride | 0.9 g |
| Sodium dihydrogen phosphate dihydrate | 0.1 g |
| Benzalkonium chloride | 0.005 g |
| 0.1 N Sodium hydroxide | q.s. to make pH 7.0 |
| Purified water | q.s. to make 100 ml. |

Polyvinylpyrrolidone, sodium chloride, sodium dihydrogen phosphate dihydrate and benzalkonium chloride were added to about 80 ml of purified water and dissolution was effected. The pH was adjusted to 7 by adding 0.1N sodium hydroxide. Fluorometholone was added and uniform suspension was effected ultrasonically. The whole volume was made 100 ml by adding purified water. A fluorometholone suspension ophthalmic preparation was thus prepared.

EXAMPLE 5
Ophthalmic preparation

| | |
|---|---|
| Sulfamonomethoxine | 0.1 g |
| Hydroxypropylmethylcellulose | 0.001 g |
| Sodium acetate | 0.1 g |
| Benzalkonium chloride | 0.005 g |
| Sodium chloride | 0.9 g |
| 0.1 N Hydrochloric acid | q.s. to make pH 5.0 |
| Purified water | q.s. to make 100 ml. |

Hydroxypropylmethylcellulose was dissolved in about 80 ml of purified water by effecting dispersion with warming, followed by cooling to room temperature. Sodium chloride, sodium acetate and benzalkonium chloride were added and dissolution was effected. The pH was adjusted to 5 by adding hydrochloric acid. Sulfamonomethoxine was added and uniform suspension was effected by means of a mill. The whole amount was made 100 ml by adding purified water. A sulfamonomethoxine suspension ophthalmic preparation was thus prepared.

EXAMPLE 6
Nasal drops

| | |
|---|---|
| Hydrocortisone acetate | 0.1 g |
| Hydroxypropylmethylcellulose | 0.0008 g |
| Sodium dihydrogen phosphate | 0.1 g |
| Methylparaben | 0.026 g |
| Propylparaben | 0.014 g |
| Concentrated glycerin | 2.6 g |
| 0.1 N Sodium hydroxide | q.s. to make pH 7.0 |
| Purified water | q.s. to make 100 ml. |

Methylparaben and propylparaben were dissolved in about 80 ml of purified water with warming. Hydroxypropylmethylcellulose was dispersed in the warm solution for effecting dissolution, followed by cooling to room temperature. Concentrated glycerin and sodium dihydrogen phosphate were added and dissolution was effected. The pH was adjusted to 7 by adding sodium hydroxide. Hydrocortisone acetate was added and uniform suspension was effected using a mixer. The whole volume was made 100 ml by adding purified water. A hydrocortisone acetate suspension for nasal application was thus prepared.

EXAMPLE 7
Parenteral preparation (injection)

| | |
|---|---|
| Estradiol benzoate | 5.0 g |
| Hydroxypropylcellulose | 0.03 g |
| Chlorobutanol | 0.3 g |
| Sodium chloride | 0.9 g |
| Purified water | q.s. to make 100 ml. |

Chlorobutanol was dissolved in about 80 ml of purified water with warming. Hydroxypropylcellulose was dissolved in the solution by effecting dispersion with warming, followed by cooling to room temperature. Sodium chloride was added for dissolution, estradiol benzoate was added, and uniform suspension was effected using a homogenizer. The whole volume was made 100 ml by adding purified water. An estradiol benzoate suspension for parenteral administration was thus prepared.

EXAMPLE 8
Preparation for oral administration

| | |
|---|---|
| Mefenamic acid | 3.0 g |
| Methylcellulose | 0.01 g |
| Sorbitol | 20 g |
| 5% Ethylparaben solution | 1 ml |
| Purified water | q.s. to make 100 ml. |

Methylcellulose was dissolved in about 50 ml of purified water by effecting dispersion with warming, followed by cooling to room temperature. Sorbitol and 5% ethylparaben solution were added for dissolution. Mefenamic acid was added and uniform suspension was effected using a homogenizer. The whole volume was made 100 ml by adding purified water. A mefenamic acid suspension for oral administration was thus prepared.

EXAMPLE 9
Lotion

| | |
|---|---|
| Indomethacin | 7.5 g |
| Hydroxypropylcellulose | 0.04 g |
| dl-Camphor | 0.5 g |
| Purified water | q.s. to make 100 ml. |

Hydroxypropylcellulose was dissolved in about 50 ml of purified water by effecting dispersion with warming, followed by cooling to room temperature. dl-Camphor was added for dissolution. Indomethacin was added and uniform suspension was effected ultrasonically. The whole volume was made 100 ml by adding purified water. An indomethacin suspension lotion was thus prepared.

INDUSTRIAL APPLICABILITY

The aqueous suspension of the present invention has good redispersibility and therefore can be utilized as an excellent aqueous suspension preparation, for example ophthalmic preparation, nasal drops, parenteral preparation, oral preparation, lotion or the like.

What is claimed is:

1. A method of reducing the redispersion time of an ophthalmic aqueous suspension, which comprises mixing fluorometholone together with hydroxypropylmethyl cellulose in a concentration range of 0.0001 to less than 0.01 % (w/v), wherein the redispersion time of said suspension is reduced, in comparison to the redispersion time of an identical suspension except having a content of hydroxypropylmethyl cellulose in a concentration range of less than 0.0001 or over 0.01 % (w/v), and wherein said redispersed suspension is a uniform suspension without aggregation of suspended particles.

2. The method of claim 1, wherein the ratio of the hydroxypropylmethyl cellulose to fluorometholone is 0.0001 to 0.2 part by weight of the former to 1 part by weight of the latter.

3. The method of claim 1, wherein the concentration of fluorometholone is 0.01 to 10% (w/v).

4. A method of reducing the redispersion time of an ophthalmic aqueous suspension, which comprises mixing fluorometholone together with methyleflulose in a concentration range of 0.0001 to less than 0.01 % (w/v), wherein the redispersion time of said suspension is reduced, in comparison to the redispersion time of an identical suspension except having a content of methylcellulose in a concentration range of less than 0.0001 or over 0.01 % (w/v), and wherein said redispersed suspension is a uniform suspension without aggregation of suspended particles.

5. The method of claim 4, wherein the ratio of the methylcellulose to fluorometholone is 0.0001 to 0.2 part by weight of the former to 1 part by weight of the latter.

6. The method of claim 4, wherein the concentration of fluorometholone is 0.01 to 10% (w/v).

7. A method of reducing the redispersion time of an ophthalmic aqueous suspension, which comprises mixing fluorometholone together with polyvinylpyrrolidone in a concentration range of 0.0001 to less than 0.01 % (w/v), wherein the redispersion time of said suspension is reduced, in comparison to the redispersion time of an identical suspension except having a content of polyvinylpyrrolidone in a concentration range of less than 0.0001 or over 0.01 % (w/v), and wherein said redispersed suspension is a uniform suspension without aggregation of suspended particles.

8. The method of claim 7, wherein the ratio of the polyvinylpyrrolidone to fluorometholone is 0.0001 to 0.2 part by weight of the former to 1 part by weight of the latter.

9. The method of claim 7, wherein the concentration of fluorometholone is 0.01 to 10% (w/v).

* * * * *